United States Patent [19]

DeVaughn

[11] 4,082,614

[45] Apr. 4, 1978

[54] MEANS FOR CONVEYING PATHOLOGICAL SPECIMENS SAFELY TO PLACES OF IDENTIFICATION

[75] Inventor: Donald H. DeVaughn, San Francisco, Calif.

[73] Assignee: Bio-Syn, Inc., San Francisco, Calif.

[21] Appl. No.: 639,156

[22] Filed: Dec. 10, 1975

[51] Int. Cl.² .............................................. C12B 1/00
[52] U.S. Cl. .................................... 195/139; 195/126
[58] Field of Search ...................... 195/139, 127, 126

[56] References Cited

U.S. PATENT DOCUMENTS

| | | | |
|---|---|---|---|
| 3,248,302 | 4/1966 | Mackin | 195/126 |
| 3,308,039 | 3/1967 | Nelson | 195/139 |
| 3,563,859 | 2/1971 | Fink | 195/139 |
| 3,616,263 | 10/1971 | Anandam | 195/139 |
| 3,616,265 | 10/1971 | Calabrese et al. | 195/139 |
| 3,817,839 | 6/1974 | Warren | 195/139 |
| 3,849,256 | 11/1974 | Linder | 195/139 |
| 3,876,503 | 8/1975 | Mennen | 195/127 |
| 3,915,806 | 10/1975 | Horlach | 195/127 |
| 3,961,696 | 6/1976 | Bowie | 195/127 |

*Primary Examiner*—Alvin E. Tanenholtz
*Attorney, Agent, or Firm*—Flehr, Hohbach, Test, Albritton & Herbert

[57] ABSTRACT

A container for transferring pathogenic micro-organisms directly from the patient to the place of identification while keeping them alive whether they are obligate or facultative organisms. It comprises an enclosure having an open end, a carrier structure presenting a pair of culture areas supporting different nutrients thereon slidably received in said enclosure through said open end thereof, a hollow stopper adapted to hermetically seal the open end of said enclosure, and means in the interior of said stopper operable to release an oxygen-absorbing medium so as to establish an oxygen free atmosphere in the interior of the enclosure. The container is made of heat resistant transparent material so that it can be placed into a culturing chamber and that culture formations on the nutrient supporting areas of the carrier structure can be observed directly without need to remove the carrier structure from the enclosure.

4 Claims, 6 Drawing Figures

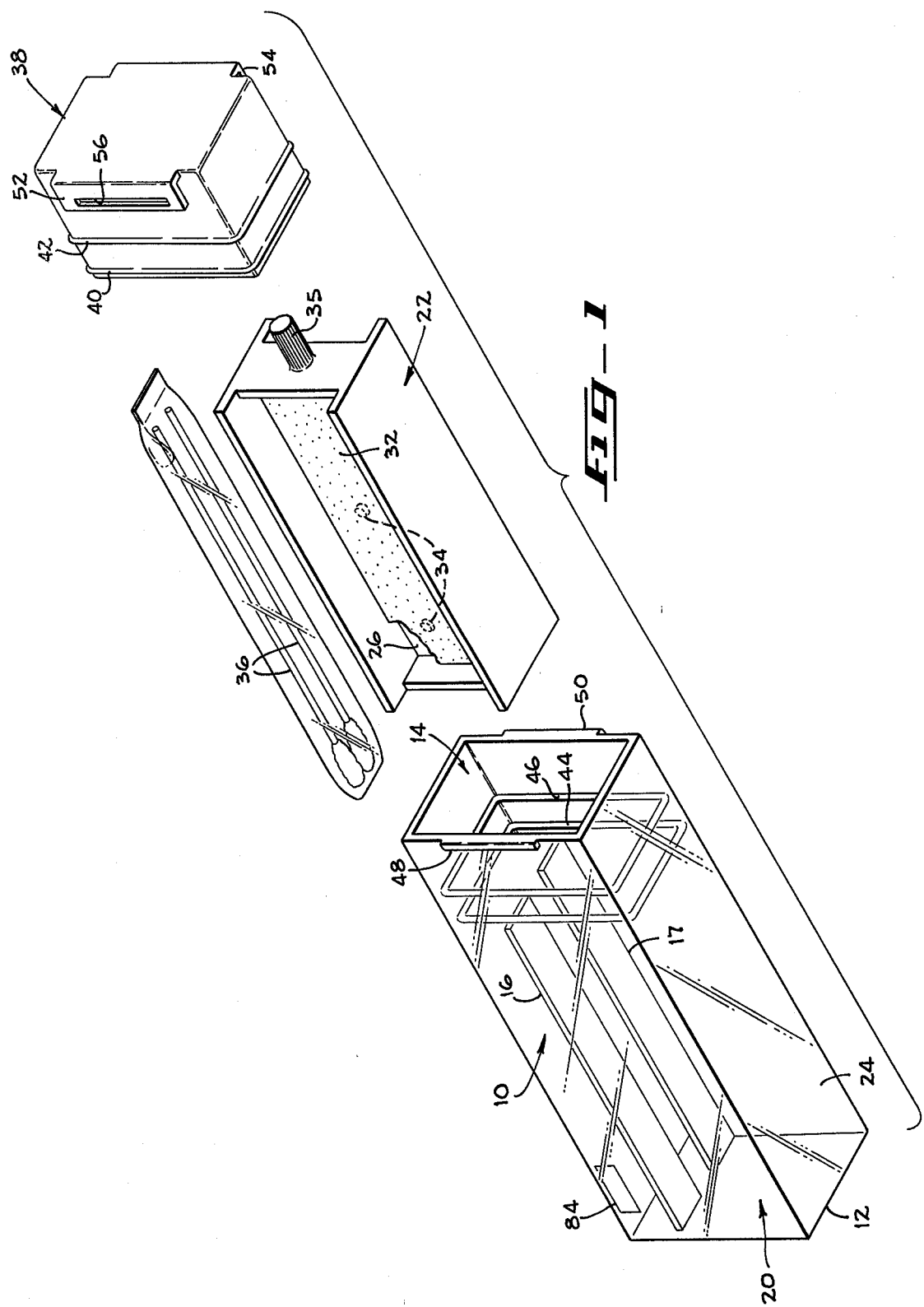

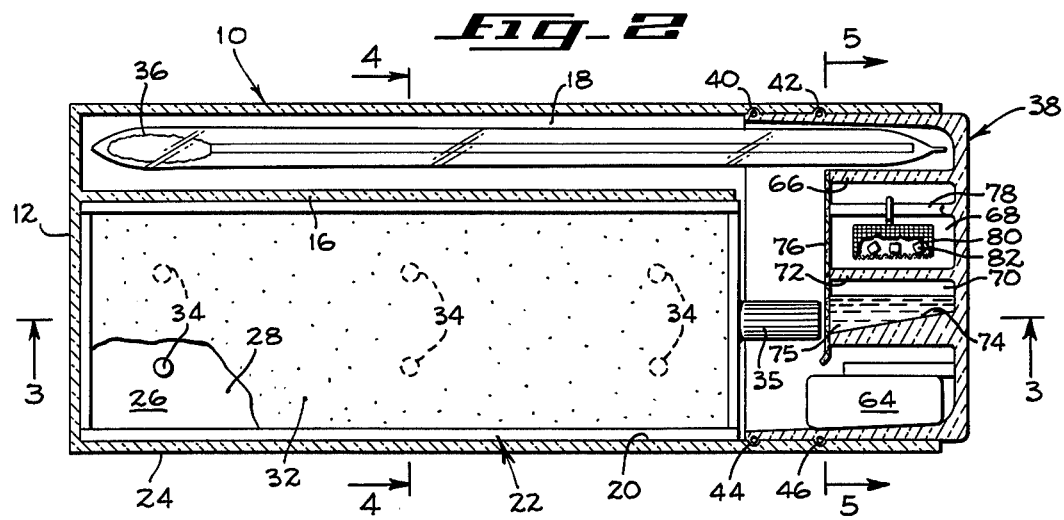
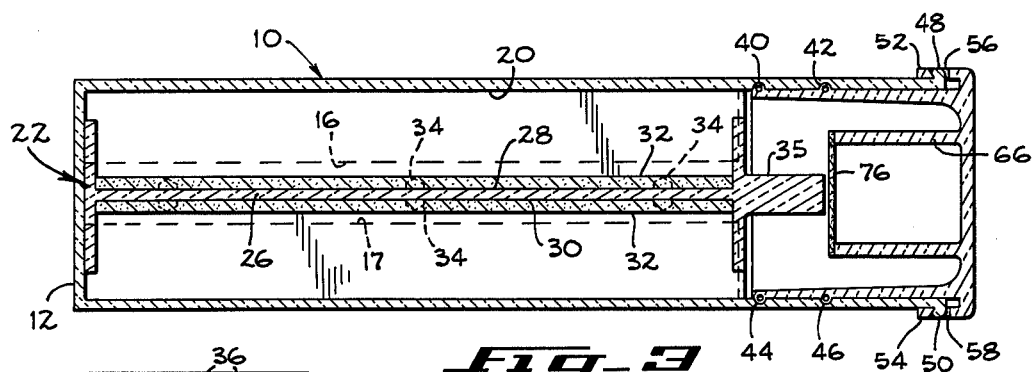
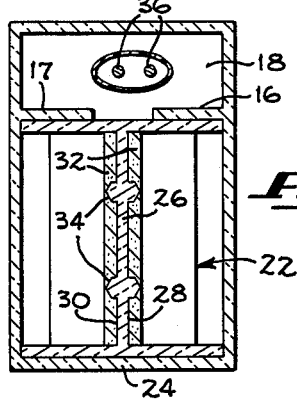
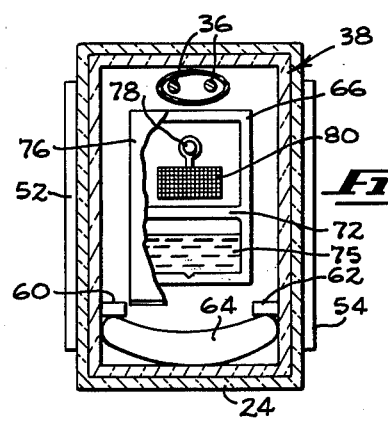
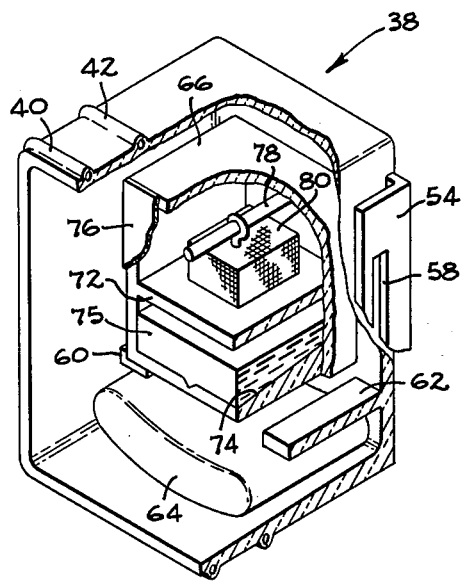

MEANS FOR CONVEYING PATHOLOGICAL SPECIMENS SAFELY TO PLACES OF IDENTIFICATION

BACKGROUND OF THE INVENTION

The present invention relates to the problem of conveying pathological specimens in live condition to the place where they can be cultured and identified.

Most pathological micro-organisms are very sensitive to environmental conditions other than the place of infection, and they die quickly when removed therefrom. For the purpose of identification they must be subjected to moderate heat on a suitable nutrient medium to form cultures or colonies that can be identified by their characteristic form. At present they are collected at the source of infection with gassed-out swabs or tubes to be taken to the place of identification, but frequently they die during the transport before they reach the place of identification, and they are therefore no longer able to form colonies or cultures.

Many pathogenic micro-organisms die quickly when exposed to oxygen. These are called obligate anerobic micro-organisms. Others tolerate oxygen; these are called facultative anerobic organism or micro-aerophilic organisms, but often they require special nutrients to survive during transportation. Many are vulnerable to the life processes of other micro-organisms that are ever present in the air or in the nutrients on which they are supposed to thrive, and they have to be protected from the adverse effects of competitive micro-organisms. Thus, certain ever-present micro-organisms reproduce within 20 minutes and will kill obligate anerobic micro-organisms by over growth.

OBJECTS OF THE INVENTION

The principle object of the invention is to simplify the complicated, cumberson, costly and time-consuming manner and method of taking specimens of pathogenic micro-organisms from a source, such as a patient, and identifying them without danger that they may die during transport before they can be identified.

Another object of the invention is to provide simple and inexpensive, portable carrier means that can readily be taken to the source of infection such as a patient to be inoculated and which will sustain the life of specimens of pathogenic micro-organisms whether facultative or obligate.

Still another object of the invention is to provide a vessel of the type referred to, within which the process of identification may be started and carried through without the necessity of removing the specimens to a different apparatus.

Still another object of the invention is to provide a vessel, of the type referred to, from which the specimens do not have to be removed for culturization.

Yet another object is to provide a container, of the type described which permits inspection of the culture formations of the specimens without need to remove them from the container.

An additional object of the invention is to provide a compact specimen-conveying vessel, of the type referred to, that is of simple and compact construction.

SUMMARY OF THE INVENTION

The invention comprises an enclosure of heat resistant transparent material within which is slidably received a carrier structure that presents culture-carrying surfaces adapted to support a plurality of different nutrients for pathogenic micro-organisms. The enclosure can be hermetically sealed by a hollow stopper or closure cap that contains means operable to release oxygen absorbing gasses so that an oxygen-free atmosphere may be established within the enclosure. By means of the described device pathogenic specimens may be transferred directly on to the different mutrients, are protected from the adverse effect of oxygen and may be cultured by subjecting the device to moderately elevated temperatures without need to transfer them to a special culturing center. In the enclosure the micro-organisms may be identified by observing the culture formations on the nutrient supporting areas of the carrier structure through the transparent walls of the enclosure. Thus, handling of the specimens and exposure to a hostile atmosphere is reduced to a minimum, time is saved because culturization commences almost immediately, and there is a great saving in equipment because no containers are required to protect inoculated swabs during transport and no special culturization center is necessary to which the specimens have to be taken nor are special dishes needed into which the micro-organisms have to be transferred for culturization.

BRIEF DESCRIPTION OF THE DRAWINGS

FIG. 1 is a perspective of the complete device of the invention in disassembled condition.

FIG. 2 is an elevation of a central longitudinal vertical section of the device of the invention in assembled condition standing on one of its narrow sides.

FIG. 3 is a section of the device of the invention taken along line 3 — 3 of FIG. 2 and viewed in the direction of the arrows associated with said line;

FIG. 4 is a cross-section through the device of the invention taken along line 4 — 4 of FIG. 2 and viewed in the direction of the arrows associated with said line;

FIG. 5 is another cross-section through the device of the invention taken along line 5 — 5 of FIG. 2 and viewed in the direction of the arrows associated with said line; and FIG. 6 is a perspective of the hollow stopper by means of which the device of my invention may be closed.

The device of the invention comprises an enclosure 10 of roughly rectangular cross-section that is preferrably made of a transparent heat resistant plastic such as polystyrene. One of the ends of the enclosure is closed as shown at 12 and the other end 14 is open (FIG. 1). Vertically aligned partitioning sections 16 and 17 divide the space within the enclosure into two compartments 18 and 20. Compartment 20 is the larger one and is adapted to slidably receive a carrier structure 22. The carrier structure 22 has the cross-sectional contour of an H and is of a size to fit snugly into the space defined by and between the outer side wall 24 of the enclosure 10 and the vertically aligned wall sections or partitions 16 and 17, namely compartment 20. The portion 26 of slide 22 corresponding to the cross bar of the "H" forms two oppositely located surfaces 28 and 30, respectively, each adapted to carry a layer of nutrient 32. To assure that a layer of nutrient deposited upon these surfaces may stay on these surfaces, they are provided with pegs or plugs 34 as shown. In practical use these surfaces will carry different kinds of nutrients, for instance, an all purpose nutrient such that will nourish most pathogenic micro-organism whether they be faculative or obligate, and another one that is specially designed to protect and promote the growth of obligate anerobic organisms. For this purpose the second nutrient may contain special antibiotics that destroy or at least inhibit certain micro-organisms which reproduce rapidly and which are ever present in the atmosphere and may be present in body fluids. The carrier structure 22 may be provided with a suitable handle 35 (FIGS. 1, 2 and 3) to facilitate its withdrawal from and reinsertion into the enclosure 10. The second and smaller compartment 18 of the enclosure 10 is adapted to receive and hold a number of gassed-out swabs 36 which the technician will need at the source of an infection to transfer specimens from the source onto the nutrients upon the upper and lower surfaces of the cross bar portion 26 of the carrier slide without impairment of their viability.

The open end of the enclosure 10 may be hermetically sealed by a cap or stopper such as shown at 38 in FIGS. 1, 2, 3 and 6. In the exemplary embodiment of the invention that I am about to describe the stopper 38 has the form of a hollow cap of rectangular cross-section that fits snugly into the open end 14 of the enclosure; and along its outer surface near the edge of its open end it is provided with a pair of thin-walled circumferential tubular bands 40 and 42 of plastic material. When the stopper 38 is pushed into the open end 24 of enclosure 10, as shown in FIGS. 2 and 3, the tubular bands 40 and 42 snap into circumferential grooves 44 and 46 in the inner surface of the enclosure 10 (FIG. 1), and thus separate the interior of the enclosure hermetically from the outside atmosphere. To hold the stopper in its enclosure-closing position releasable latch means may be provided. Thus, near its open end the enclosure 10 carries on its outside a pair of oppositely located bar-shaped latching members 48 and 50 (FIG. 1) and the stopper 38 is provided near its end wall with a pair of correspondingly located latches 52 and 54 (FIGS. 1 and 6) that may have the form of short angle bars which project from the outer surface of the stopper near its closed bottom end and whose horizontal flanges are provided with latching slots 56 and 58. When the stopper is pushed into the open end 14 of the enclosure 10 and the latch bars 48 and 50 on the outside of the enclosure slip underneath the horizontal flanges of angle bars 52 and 54, they snap into the slots 56 and 58 respectively and the stopper 38 is dependably held in its enclosure-closing condition.

The hollow stopper 38 contains means that may be activated to release oxygen-binding gasses in sufficient quantities so that upon closing the open end of the enclosure the total inner space thereof including the hollow interior of the stopper will be free of all oxygen. In the exemplary embodiment of the invention which I am about to describe a pair of short fillets 60 and 62 rise from the floor or bottom of the hollow stopper a limited distance above one of its narrow sides. These fillets are intended to hold down a package of chemicals 64. Above said fillets a box-like structure 66 is secured to the floor of the hollow stopper. This box-like structure is divided into two compartments 68 and 70 by a partition 72 (FIGS. 2 and 6). The lower compartment 70 has a floor that forms a ramp or slide 74 (FIG. 2) which leads into the space above the package 64 held by the fillets 60 and 62. It is intended to contain water as indicated at 75 in FIGS. 2 and 6 which is retained in the compartment by a detachable tag or flap 76 of plastic material that may be pulled away by the user of the device before he closes the enclosure 10 with stopper 38. From the floor of the upper compartment 76 of box 66 rises a post 78 (FIG. 6) from which is suspended a screen cage or basket 80 that contains catalyst material for the reaction that is to take place in the interior of stopper 38 after the water has been released from compartment 70 onto the package of chemicals 64. These catalysts are represented by pellets 82.

In an exemplary embodiment the packet of chemicals may contain 45 mg of citric acid ($C_6O_7H_8$), 91 mg of sodium bicarbonate ($NaHCO_3$), and 35 mg of sodium borohydride ($NaBH_4$). To activate the system, the tab 76 is pulled and 1 ml of water is emptied over the dry chemicals. The stopper 38 is then applied to the enclosure 10 to close it in an air-tight manner.

Several chemical reactions take place when the water is added to the dry chemicals. The first reactions that occur are ionization of two of the compounds. Solid sodium borohydride ($NaBH_4$) dissolves completely to form sodium ions and borohydride ions, ($NaBH_4(s)$ $NA^+_{(aq)} + BH_4^-_{(aq)}$). At the same time sodium bicarbonate dissolves to form sodium and bicarbonate ions, ($NaHCO_3(s)$ $Na^+_{(aq)} + HCO_3^-_{(aq)}$). Critric acid undergoes a dissociation to produce $H^+$ ions when it dissolves in water. These ions combine with the bicarbonate ions to form carbon dioxide gas and water $H^+_{(aq)} + HCO_3^-_{(aq)}$ $H_2O + CO_{2(gas)}$. The excess hydrogen ions $H^+$ are reduced by the $BH_4^-$ ions to produce hydrogen gas. The hydrogen gas reacts with oxygen trapped within the enclosure. This reaction proceeds faster when a catalyst is present such as palladium on alumina. When this reaction has been complete a methylene blue indicator on filter paper located at a suitable place in the enclosure as indicated at 84 in FIG. 1 turns from blue to white demonstrating tht oxygen in the air within the enclosure 10 has been removed and replaced with carbon dioxide and residual hydrogen gasses.

METHOD OF USE

Formerly when pathogenic micro-organisms or other micro-organisms had to be identified, specimens were taken at the source such as a patient, by means of gassed-out swabs which were placed into small gassed-out tubular containers. The containers were closed and rushed to a central place of identification. Here they were transferred onto Petri dishes, i.e. shallow dishes provided with layers of different nutrients which were inoculated with the swabs, whereupon the inoculated dishes were placed into incubators i.e. ovens in which the inoculated nutrients were subjected to moderate temperatures, such as +35° C for extended periods of time. From time to time the Petri dishes were withdrawn from the incubator to observe whether cultures had formed or were forming, and to study the character and nature of these cultures. This procedure was complicated, costly and unreliable, and required costly equipment, such as the Petri dishes and a central incubation area.

Many of the obligate anerobic micro-organism died during transport of the swabs and transfer onto the Petri dishes due to exposure to oxygen, and could no longer be cultured in the incubators rendering the tests incomplete and unreliable. In contradistinction the device of the invention is easily portable, it can be taken directly to the source, for instance a patient, where technicians remove the stopper, pull the double tray 22 from the enclosure, withdraw the swabs 36, inoculate them directly at the source, use the inoculated swabs immediately to inoculate the nutrients on both sides of the tray, return the tray to the enclosure, pull the tab 76 to initiate the above described chemical reactions and apply the stopper to the enclosure with a minimum of exposure of the specimens to oxygen. The swabs may now be discarded. No special containers for the hazardous transport to the places of incubation and identification are needed. After the oxygen-binding means in the stopper have been activated by pulling the flap 76 and the stopper has been applied to seal the enclosure, the enclosure becomes clear of any free oxygen. Thus, the device of the invention with the inoculated nutrients enclosed therein may now be taken to a central place for identification without any undue rush because the specimens are protected from exposure to oxygen, in fact the micro-organism to be identified may begin to form cultures during the transport so that much time is saved. At the central place for identification the inoculated specimens do not have to be transferred onto Petri dishes, in fact no Petri dishes are needed at all. The device of the invention with the inoculation specimens contained therein is simply placed as a whole into the incubator. Thus, again the specimens are not exposed to oxygen, and time, labor and equipment are saved. During the incubation process, it is unnecessary to remove the specimens for inspection to determine whether cultures have formed or are being formed. Due to the fact that both the nutrient-carrying areas of the carrier slide 22 are flat and clearly visible through the transparent top and bottom walls of the enclosure, it is unnecessary to remove the carrier slide from the enclosure for observation and in this manner expose the specimens to a hostile atmosphere. Again this does not only mean increased protection of the specimens, it also means a saving in time and labor.

What I claim is:

1. A portable culturing device for both obligate and facultative micro-organisms comprising an elongated enclosure of transparent heat resistant material having an open end; partitioning means dividing said enclosure into two vertically aligned compartments one of which contains a tool for transferring specimens; a carrier structure having a flat area containing layers of nutrient slidably received in the other one of said compartments through the open end of said enclosure, said carrier structure being of H-shaped cross-sectional contour with the upper and lower areas of the cross bar of the H forming culturing areas and with all opposed edges in slidable contact with the walls of said second compartment; closure means adapted to hermetically seal said enclosure; and means within said closure means operable to bind free oxygen within said enclosure and to generate carbon dioxide to replace the oxygen removed by the oxygen binding means.

2. A device as claimed in claim 1 wherein said tool is a gassed-out swab.

3. A device as claimed in claim 1 in which said closure means has a plurality of separate compartments formed as an integral part thereof adapted for storing chemical compounds capable of reaction to produce the oxygen-binding gas and capable of generating carbon dioxide.

4. A device as claimed in claim 3 in which at least one of said compartments of said closure means is sealed by a pull tab to store said chemical compounds prior to use with removal of the tab causing the compounds to contact and produce the oxygen-binding gas and carbon oxide.

* * * * *